United States Patent
Mirza

(10) Patent No.: US 10,272,024 B1
(45) Date of Patent: Apr. 30, 2019

(54) METHODS FOR ADMINISTRATION OF COSMETIC AND MEDICAL AGENTS

(71) Applicant: Muhammad Mirza, Cedar Grove, NJ (US)

(72) Inventor: Muhammad Mirza, Cedar Grove, NJ (US)

( * ) Notice: Subject to any disclaimer, the term of this patent is extended or adjusted under 35 U.S.C. 154(b) by 141 days.

(21) Appl. No.: 15/361,931

(22) Filed: Nov. 28, 2016

(51) Int. Cl.
| | |
|---|---|
| *A61K 8/60* | (2006.01) |
| *A61K 8/65* | (2006.01) |
| *A61K 8/81* | (2006.01) |
| *A61K 8/85* | (2006.01) |
| *A61K 9/00* | (2006.01) |
| *A61K 38/48* | (2006.01) |
| *A61Q 19/00* | (2006.01) |
| *A61Q 19/08* | (2006.01) |
| *A61K 8/66* | (2006.01) |

(52) U.S. Cl.
CPC .................. *A61K 8/66* (2013.01); *A61K 8/60* (2013.01); *A61K 8/65* (2013.01); *A61K 8/8147* (2013.01); *A61K 8/85* (2013.01); *A61K 9/0019* (2013.01); *A61K 38/4893* (2013.01); *A61Q 19/00* (2013.01); *A61Q 19/08* (2013.01); *C12Y 304/24069* (2013.01)

(58) Field of Classification Search
CPC .. A61K 38/4893; A61K 9/0019; A61Q 19/00; A61Q 19/08; C12Y 304/24069
See application file for complete search history.

(56) References Cited

U.S. PATENT DOCUMENTS

| | | |
|---|---|---|
| 9,433,463 B2 | 9/2016 | Wolf et al. |
| 2002/0028765 A1 | 3/2002 | Maurer |
| 2014/0121636 A1* | 5/2014 | Boyden et al. |
| 2016/0263202 A1 | 9/2016 | Blumenfeld et al. |

FOREIGN PATENT DOCUMENTS

| | | |
|---|---|---|
| DE | 69929361 | 9/2006 |
| WO | WO200024419 | 5/2000 |

OTHER PUBLICATIONS

Chytra V. Anand, J Cutan Aesthet Surg., 2010, vol. 3, No. 1, p. 23-24.*
Tremaine et al., Botulinum toxin type A for the management of glabellar rhytids, Clin Cosmet Investig Dermatol, Mar. 2010, vol. 3, pp. 15-23.

* cited by examiner

*Primary Examiner* — Kade Ariani
(74) *Attorney, Agent, or Firm* — Dentons US LLP

(57) ABSTRACT

The present disclosure provides improved methods for administration or application of cosmetic or medical agents, including, but not limited to, dermal fillers and Botox-type injectable agents.

9 Claims, 2 Drawing Sheets

METHODS FOR ADMINISTRATION OF COSMETIC AND MEDICAL AGENTS

TECHNICAL FIELD

This disclosure relates to a field of cosmetic treatment procedures and certain medical procedures, and more specifically to improved methods for administration of cosmetic agents, including, but not limited to, Botox-type injectable agents and dermal fillers.

BACKGROUND

A conventional method of cosmetic procedures involving an administration of a cosmetic agent, such as a Botox-type cosmetic agent and/or a dermal filler, or certain medical procedures involving the administration of a medical agent such as a Botox-type medical agent, is to have a patient seated and reclined. This allows for comfort and support for the patient, as well as proper lighting and the least amount of distraction for the administering physician. However, this results in relaxation of the muscles, which may hide any lines or sagging, as well as muscle definition. This creates an issue of where to treat, since the target of such cosmetic and medical procedures are such lines, sagging muscles or muscles in need of medical attention.

BRIEF SUMMARY

The present disclosure provides a method of administration of at least a first cosmetic agent to a patient in need thereof, comprising administration of the at least a first cosmetic agent to the patient while the patient is in a standing position. Such methods are also referred to herein as "cosmetic procedures" or "cosmetic methods." In certain embodiments, the at least a first cosmetic agent is a dermal filler. In some embodiments the dermal filler comprises hyaluronic acid. Examples of such dermal fillers include, but are not limited to, Juvederm®, Juvederm® Voluma XC, Juvederm® Ultra XC, Juvederm® Ultra Plus XC, Juvederm® Volbella®, Restylane®, Restylane® Silk, and Belotero®. In other embodiments the dermal filler comprises poly-L-lactic acid. A non-limiting example of such a dermal filler is Sculptra® Aesthetic. In yet other embodiments the dermal filler comprises collagen and polymethylmethacrylate. Examples of such dermal fillers include, but are not limited to, Bellafill® and ArteFill®. In additional embodiments any combination of the above dermal fillers can be administered to the patient.

In further embodiments the at least a first cosmetic agent stimulates collagen production in the patient. Examples of such cosmetic agents include, but are not limited to, Radiesse® and Radiesse® (+). In still further embodiments the at least a first cosmetic agent comprises a botulinum toxin type A. Examples of such cosmetic agents include, but are not limited to, Botox®, Dysport®, or Xeomin®. In additional embodiments the at least a first cosmetic agent comprises platelet rich plasma. In particular embodiments, the platelet rich plasma is obtained from the patient. In another embodiment the at least a first cosmetic agent is at least a first polydioxanone (PDO) thread. In certain embodiments the at least a first PDO thread is a smooth thread or a barbed thread. In other embodiments the at least a first cosmetic agent is ultrasound or a micro-needling system.

Some of the cosmetic procedures or methods disclosed herein comprise administration of a combination of two or more cosmetic agents, also referred to as a plurality of cosmetic agents, for example at least a first cosmetic agent and at least a second cosmetic agent, to the patient. In some of these embodiments the at least a first cosmetic agent is a dermal filler and the at least a second cosmetic agent comprises Botulinum toxin type A, the at least a first cosmetic agent is a dermal filler and the at least a second cosmetic agent comprises platelet rich plasma, or the at least a first cosmetic agent comprises platelet rich plasma and the at least a second cosmetic agent is a micro-needling system.

In certain embodiments the at least a first cosmetic agent is administered to any area of the patient, including, but not limited to, a facial area, neck area, hand area, breast area, head area, leg area or butt area of the patient. In particular embodiments the at least a first cosmetic agent is administered to a facial area of the patient. In such embodiments the at least a first cosmetic agent is administered to any part of the facial area of the patient, including, but not limited to, at least a first lip, at least a first cheek, at least a first eyebrow, a nose, a chin or a jaw of the patient. In further embodiments the at least a first cosmetic agent is administered to two or more areas of the patient, or in other words a plurality of areas of the patient.

The present disclosure also provides a method of treating a medical condition in a patient, comprising administration a therapeutically effective amount of a medical agent, such as a Botox-type injectable medical agent, to the patient while the patient is in a standing position. As used herein, the term "therapeutically effective amount" means an amount, dosage or regimen that results in the prevention, arrest or amelioration of the medical condition. In certain embodiments the Botox-type injectable medical agent is Botox®, Dysport®, or Xeomin®. In further embodiments the medical condition is a migraine headache, tension-type headache, chronic headache, cluster headache, occipital neuralgia, cervical dystonia, blepharospasm, or pain management for fibromyalgia, increased muscle stiffness in elbow, wrist and finger muscles in a patient with upper limb spasticity, or increased muscle stiffness in calf muscles in a patient with lower limb spasticity. In additional embodiments a therapeutically effective amount of a second medical agent is administered to the patient. In some embodiments a combination or plurality of medical agents is administered to the patient.

The present disclosure additionally provides a method of treating a headache in a patient, comprising administration a therapeutically effective amount of a medical agent, for example a Botox-type injectable medical agent, to the patient while the patient is in a standing position. In certain embodiments the Botox-type injectable medical agent is Botox®, Dysport®, Xeomin®, or any combination thereof. In particular embodiments the headache is a migraine headache, tension-type headache, chronic headache, cluster headache, or occipital neuralgia.

BRIEF DESCRIPTION OF DRAWINGS

The following drawings form part of the present specification and are included to further demonstrate certain aspects of this disclosure. This disclosure may be better understood by reference to one or more of these drawings and their corresponding descriptions below, in combination with the detailed description of specific embodiments presented herein.

DETAILED DESCRIPTION

Figures 1A, 1B:
FIG. 1A and FIG. 1B: A first patient is shown in the sitting (FIG. 1A) and standing (FIG. 1B) position, highlighting the difference in appearance of the nasolabial folds in the sitting and standing position.

This disclosure provides improved methods for an administration of one or more cosmetic agents in a wide variety of cosmetic procedures, as well as improved methods for an administration of one or more medical agents in certain medical procedures. Specifically, by administering one or more cosmetic or medical agents while a patient is in a standing position results in greater accuracy in targeting and treating the lines and sagging muscles underlying the undesired anatomic details of the patient, as well as targeting and treating the muscles underlying certain medical conditions.

Age and gravity are the two worst enemies of perfect skin. Volume loss, bone loss and gravitational descend are the main effects. Structural volume loss is the loss of the shape of the face, namely, the volume of the face. As the skin sags and cellulite is erased, once plump facial features may become hollow and unattractive. Harsh sun rays, stress, child rearing and much more can cause tensed muscles, which causes the volume loss.

Functional loss, however, specifically references change in the muscles. As time passes, skin begins to sag, muscles becomes hidden and facial volume changes. The combination of these results in giving the face and other body features a different semblance. This functional loss, to some extent, can be reversed using a selection of cosmetic agents such as muscle relaxers and/or dermal fillers. In addition, certain medical conditions, including, but not limited to, migraine and other types of headaches, pain management, and muscle stiffness or spasms, can be treated using medical agents such as muscle relaxers.

In conventional methods of administration of cosmetic agents, such as dermal fillers and Botox-type agents, as well as administration of medical agents, such as Botox-type agents, the patient is seated and reclined, mainly for the comfort of the patient. However, this presents certain issues for the treating physician, as the muscles of the patient are relaxed. This makes it difficult for the physician to see exactly how the skin and muscles fall. The result of this relaxation is that the true sagging and hollowness in volume is hidden, and the musculature connected with certain medical issues may be difficult to identify. This hinders the physician in selecting exactly where and how to inject. The selection and injection process is more effective when the administering physician has a clear view of all features to be addressed. In sitting and reclining, the muscles are relaxed and do not contour to the face and other anatomical features in the same way as when the muscles are engaged.

This disclosure overcomes these and other shortcomings of current cosmetic and medical techniques for administration of cosmetic and medical agents by administration of these cosmetic and medical agents while the patient is in a standing position. Based on body hemodynamics and kinetic physiology, the functional loss and structural volume loss to be addressed by the physician is more pronounced when the patient is standing. This means that sagging, lines, wrinkles and stiff or spasming muscles are optimal and most visible to the physician. When muscles and bone structure can be clearly seen, it gives the physician a unique perspective on how to treat the problem areas most effectively. Long lasting results, although temporarily somewhat uncomfortable, are preferred.

Volume loss, as well as stiff or spasming muscles, are more pronounced when the patient is in an erect standing position. When standing face to face with the patient, the physician can see exactly where the cosmetic or medical product or agent is needed, how much is needed, what kind is needed, and how best to administer the product. Never losing sight of where wrinkles, volume loss and structural or functional loss occurs results in greater ease for the physician, and greater satisfaction for the patient.

I. Cosmetic Agents

A number of different cosmetic agents, for example chemical agents, mechanical agents and physical agents, as well as combinations of these cosmetic agents, can be used in the practice of the claimed cosmetic procedures. Although certain of these cosmetic agents are described in greater detail below, inclusion of these agents is not meant to be exhaustive of the cosmetic agents that can be used in this disclosure.

A. Botulinum Toxin Agents

A number of cosmetic agents comprising botulinum toxin type A are available for use in a variety of cosmetic procedures. In general these agents are referred to as "Botox-type injectables." Botulinum toxin type A is an acetylcholine release inhibitor and a neuromuscular blocking agent. Botulinum toxin type A blocks neuromuscular transmission by binding to acceptor sites on motor nerve terminals, entering the nerve terminals, and inhibiting the release of acetylcholine. Botulinum toxin type A produces partial chemical denervation of the muscle, resulting in a localized reduction in muscle activity.

The most popular of these agents is Botox® (onabotulinumtoxinA), which is purified botulinum toxin type A, produced from fermentation of the bacterium *Clostridium botulinum* type A, Hall Strain, and is intended for intramuscular use. It is purified from the culture solution by dialysis and a series of acid precipitations to a complex consisting of the neurotoxin, and several accessory proteins.

Another Botox-type injectable cosmetic agent is Dysport® (abobotulinumtoxinA), which in addition to abobotulinumtoxinA contains human albumin and lactose. Dysport® is a purified neurotoxin type A complex produced by fermentation of the bacterium *Clostridium botulinum* type A, Hall Strain, and is intended for intramuscular use. It is purified from the culture supernatant by a series of precipitation, dialysis, and chromatography steps. The neurotoxin complex is composed of the neurotoxin, hemagglutinin proteins and non-toxin non-hemagglutinin protein. Dysport® is a prescription injection that temporarily improves the look of moderate to severe frown lines without changing the face's overall appearance. The untreated facial muscles still work normally, allowing the patient to freely show facial expressions, such as smiling, in untreated areas. For up to four months, Dysport® works to block the signal from the nerve to the muscles, resulting in a reduction of muscle activity and temporarily preventing contraction of the muscles that cause frown lines. In general patients should not be treated with Dysport® more frequently than every 90 days.

An additional Botox-type injectable cosmetic agent is Xeomin® (incobotulinumtoxinA). Xeomin® is botulinum toxin type A produced from fermentation of Hall strain *Clostridium botulinum* serotype A, and is intended for intramuscular use. The botulinum toxin complex is purified from the culture supernatant, and then the active ingredient is separated from the proteins (hemagglutinins and non-hemagglutinins) through a series of steps yielding the active neurotoxin without accessory proteins. Xeomin® contains botulinum toxin type A, human albumin and sucrose. Xeomin® is a prescription medication used in facial aesthetics to temporarily improve the appearance of moderate to severe glabellar frown lines between the eyes (glabellar lines) in adults. When a person squints or frowns, the muscles between the brows contract, causing the skin to furrow and fold. These lines that occur due to facial mimics are referred to as dynamic lines. Over time, as skin ages and loses some of its elasticity, these repeated contractions can cause persistent frown lines. Xeomin® is used in facial aesthetic treatment to treat dynamic lines like glabellar frown lines by acting on nerve endings in muscles to prevent muscle fibers from contracting. By reducing these contractions, Xeomin® can temporarily reduce the frown lines on the forehead between the eyes.

B. Injectable Dermal Fillers

Certain cosmetic agents are known as injectable dermal fillers, or dermal fillers, and can be made with a variety of different chemical agents, including, but not limited to, hyaluronic acid (HA), calcium hydroxylapatite, poly-L-lactic acid (PLLA), and polymethylmethacrylate (PMMA). Hyaluronic acid is a naturally occurring substance that is normally present in skin. It helps keep skin plump and hydrated. HA fillers are typically soft and gel-like. The results are temporary, lasting 6 to 12 months or longer before the body gradually and naturally absorbs the particles. Certain HA fillers are infused with lidocaine to help minimize discomfort during and after treatment. HA fillers currently approved by the United States Food and Drug Administration (FDA) include Juvederm® Ultra, Juvederm® Ultra Plus, Juvederm® Voluma® XC, Juvederm® Ultra XC, Juvederm® Ultra Plus XC, Juvederm® Volbella®, Restylane®, Restylane® Silk, or Belotero®.

Juvederm® Voluma® XC is a sterile, biodegradable, non-pyrogenic, viscoelastic, clear, colorless, homogenized gel implant, comprising crosslinked hyaluronic acid (HA) produced by *Streptococcus equi* bacteria and 0.3% lidocaine in a physiologic buffer. Juvéderm® Voluma® XC injectable gel is indicated for deep (subcutaneous and/or supraperiosteal) injection for cheek augmentation, to correct age-related volume deficit in the mid-face in adults over the age of 21.

Juvederm® Ultra and Juvederm® Ultra Plus are sterile, biodegradable, non-pyrogenic, viscoelastic, clear, colorless, homogeneous gel implants, comprising cross-linked hyaluronic acid (HA) produced by *Streptococcus* species of bacteria, and a physiologic buffer. Juvederm® Ultra XC, Juvederm® Ultra Plus XC and Juvederm® Volbella® XC are sterile, biodegradable, non-pyrogenic, viscoelastic, clear, colorless, homogeneous gel implants, comprising cross-linked hyaluronic acid (HA) produced by *Streptococcus* species of bacteria, and 0.3% lidocaine in a physiologic buffer. Juvederm® Ultra XC and Juvederm® Ultra Plus XC are an effective and safe, non-surgical treatment used to smooth the skin and return facial contours to their naturally youthful and healthy state. They stimulate collagen production in skin and retention of water, instantly restoring unwanted lines, enhancing lips, cheeks, and jaw-line as well as other areas. Juvederm® Ultra XC provides versatility in contouring and volumizing facial wrinkles and folds. Juvederm® Ultra Plus XC is a more highly cross-linked, robust formula for the volumizing and correction of deeper folds and wrinkles. Juvéderm® Ultra XC has also been approved by the FDA for lip treatments. Juvéderm® Ultra smooths out and fills lips, giving a very natural look. Oftentimes, patients only need one treatment in order to receive the results they desire. Juvéderm® activates almost instantly in the applied areas, and the results are long lasting, usually up to about a year. Juvéderm® treatments are also effective for rolling and boxcar acne scars, as well as other types of acne scars, such as ice pick, hypertonic and keloid acne scars. The number of Juvéderm® treatments that a person will require will depend on the severity of the scars, as well as a person's facial anatomy. Patients tend to see physical results from Juvéderm® right away following the injections, but it usually takes a few months to see lasting results. When a patient receives Juvéderm® treatments, a numbing cream will be applied to decrease the pain associated with Juvéderm® shots, which is usually very minimal. Ice may also be applied before the injections are given. After the injections have been administered, ice is typically reapplied, and minimal bruising may take place for two to seven days. Juvederm® Volbella® is designed for lip augmentation and correction of perioral rhytids, wrinkles that form around the mouth. It has also been found to boost fullness in the lips and soften perioral lines. It has been proven to correct severe facial wrinkles, such as laugh lines, and is ideal for deep injection in the cheek to restore volume loss.

Restylane® is a gel of hyaluronic acid generated by *Streptococcus* species of bacteria, chemically crosslinked with 1,4-butanediol diglycidyl ether (BDDE), stabilized and suspended in phosphate buffered saline at pH 7. Restylane® Silk is the same as Restylane®, except that is further comprises 0.3% lidocaine. Restylane® adds volume and fullness to the skin to correct moderate to severe facial wrinkles and folds, such as the lines from the nose to the corners of the mouth (nasolabial folds). Restylane® is also FDA approved for lip enhancement in patients 21 years of age and older, and can be used to treat marionette lines (the area from the corner of the mouth to the jaw line), and the corners of the mouth. Restylane® Silk is the first and only FDA-approved product specifically designed for subtle lip enhancement and the smoothing of wrinkles and lines around the mouth in patients over 21 years of age. Restylane® Silk is specifically formulated for lip enhancement and treating wrinkles surrounding the mouth.

Belotero® and Belotero® Balance are sterile, biodegradable, non-pyrogenic, viscoelastic, clear, colorless, homogenized gel implants, comprising hyaluronic acid generated by *Streptococcus* species of bacteria, chemically crosslinked with 1,4-butanediol diglycidyl ether (BDDE) in two consecutively executed reactions and reconstituted in a physiologic buffer at pH 7. Belotero® is a prescription injection that is approved to temporarily smooth out and fill in moderate-to-severe nasolabial folds (the folds or wrinkles that go from the side of the nose to the corner of the mouth). Belotero® completely integrates into the skin tissue. While some fillers are designed to rebuild facial volume and structure, Belotero® specifically treats moderate-to-severe etched-in lines and wrinkles, such as vertical lip lines above and around the lips.

Calcium hydroxylapatite is also a naturally occurring substance, found primarily in bones. When used in a filler, the calcium particles are very tiny, almost microscopic, and suspended in a smooth gel. The consistency of a calcium hydroxylapatite filler is typically thicker than that of a hyaluronic acid filler, and the results will typically last longer as well, about 12 months for most patients. Calcium hydroxylapatite is also reported to help stimulate natural collagen production, and it is typically used for deeper lines and wrinkles. Calcium hydroxylapatite fillers currently approved by the FDA include Radiesse® and Radiesse® (+). Radiesse® is a sterile, non-pyrogenic, semi-solid, cohesive implant, comprising calcium hydroxylapatite suspended in a gel carrier of sterile water, glycerin and sodium carboxymethylcellulose. Radiesse® (+) is the same as Radiesse®, except that it further comprises 0.3% lidocaine hydrochloride. Radiesse® temporarily adds volume to help smooth moderate to severe facial wrinkles and folds, such as nasolabial folds (the creases that extend from the corner of the nose to the corner of the mouth). Radiesse® is injected through a small needle and placed under the skin. Immediately, Radiesse® works to add volume under the skin and over time, the benefits of Radiesse® continue by naturally stimulating the body's own natural collagen. The natural results have been shown to last a year or more in many patients, making the treatment results both immediate and long lasting.

Poly-L-lactic acid (PLLA) is a biocompatible, biodegradable synthetic substance. It has been used for many years in a number of medical devices, such as dissolvable stitches. Poly-L-lactic acid fillers are considered "semi-permanent," as the results typically last more than 2 years, and can help stimulate collagen production. As a thicker filler material, Poly-L-lactic acid is typically used to treat deeper facial wrinkles. Poly-L-lactic acid fillers currently approved by the FDA include Sculptra® Aesthetic. Sculptra® Aesthetic comprises PLLA, carboxymethylcellulose and non-pyrogenic mannitol. Sculptra® Aesthetic provides a natural-looking appearance that is gradual and long-lasting by replacing collagen, restoring the look of fullness to shallow and deep facial wrinkles and folds. A full treatment consists of 3 injection sessions over the duration of a few months, which can vary per patient. Within the deep dermis, the skin's structure is reinforced as Sculptra® Aesthetic helps to replace lost collagen. This reinforced collagen structure provides a foundation that gradually restores the look of fullness of shallow to deep facial wrinkles and folds that has been depleted over time. Sculptra® Aesthetic gradually and subtly corrects these facial wrinkles. Results can last more than 2 years.

Polymethylmethacrylate (PMMA) is a synthetic, biocompatible substance that has been used in medicine for much of the last century. When used in dermal fillers, PMMA takes the form of a microsphere that remains beneath the skin to provide continued support, in certain embodiments for up to five years. PMMA fillers generally also contain collagen, a naturally occurring substance in the skin that provides structure and firmness. PMMA fillers currently approved by the FDA include ArteFill®, which is named Bellafill® in the United States. ArteFill® and Bellafill® are comprised of 80% purified bovine collagen, 20% PMMA microspheres, and 0.3% lidocaine. Bellafill® has been approved by the FDA as a safe and effective treatment—for up to 5 years—that produces younger-looking skin by promoting the growth of the body's own collagen. Bellafill® promotes firmer, smoother skin, thus diminishing the appearance of scars and producing an overall clearer complexion. Bellafill® replaces lost volume in the skin below the wrinkle for correction that is immediate and lasting. It restores rather than just fills for natural enduring results. In clinical studies, efficacy was observed out to 12 months, although the primary efficacy endpoint was at 6 months.

C. Additional Cosmetic Agents

Another cosmetic agent used in certain cosmetic procedures are polydioxanone (PDO) threads, which can either be smooth or barbed. Smooth threads are generally inserted vertically and horizontally by means of a cannula. The mesh pattern of the threads serves as the foundation for new collagen production as the skin reacts to the sutures by repairing itself around them. Barbed threads are generally used to produce more immediate and dramatic results. The threads are inserted under the skin and grip the skin underneath. When these threads are pulled, they tighten the skin from within, resulting in an instant lift. Again, collagen production is stimulated as the skin heals itself around the threads.

In some cosmetic procedures ultrasound is used as a non-invasive treatment specifically FDA-cleared to improve lines and wrinkles on the décolletage. One ultrasound therapy agent is Ultherapy®, which uses focused ultrasound to stimulate collagen deep within the skin, with no downtime required.

Additional cosmetic procedures use a micro-needling system. One such system is Dermapen®, which is an automated micro-needling system with a disposable tip cartridge that uses 12 micro-needles to vertically stamp the skin at high speed. This causes micro-injuries to the skin, thereby stimulating new collagen and elastin production. These micro-injuries encourage and harness the body's innate ability to regrow and repair the skin through normal physiological processes.

Platelet Rich Plasma (PRP) can also be used in certain cosmetic procedures, for example facial rejuvenation. Platelets and plasma are components of the blood are extracted from a blood sample by placing it in a spinning centrifuge, which works to separate the platelets and plasma out of the blood. Platelets are cells that work to repair damage, so when platelet rich plasma is introduced to wrinkled, scarred or uneven skin tissue, collagen growth is stimulated along with the regeneration of skin tissue, resulting in more youthful, vibrant, healthy-looking skin. PRP from a patient's own blood sample is injected into the skin, similar to how a dermal filler would be. The platelets work to repair damaged or wrinkled skin by producing more collagen, causing the skin to regenerate. New skin means that fine lines and wrinkles are reduced, along with dark circles and puffiness under the eyes, and uneven or dull skin tone.

II. Cosmetic Procedures

A wide variety of cosmetic procedures utilize Botox-type injectable agents, injectable dermal fillers, as well as additional cosmetic agents, or combinations thereof. Certain of these cosmetic procedures are detailed below.

A. Treatment with Botox-Type Injectable Agents

A variety of different cosmetic procedures utilize administration of cosmetic agents comprising botulinum toxin type A. For example, these agents can be used in adults for temporary improvement in the appearance of moderate to severe glabellar lines associated with corrugator and/or procerus muscle activity, as well as temporary improvement in the appearance of moderate to severe lateral canthal lines associated with orbicularis oculi activity. Additionally, cosmetic agents comprising botulinum toxin type A can be used to treat cervical dystonia (CD), increased muscle stiffness in elbow, wrist and finger muscles in adults with upper limb spasticity, increased muscle stiffness in calf muscles in children 2 years of age or older with lower limb spasticity, and blepharospasm.

Botox-type injectable agents comprise a purified botulinum toxin type A protein that causes tensed muscles to relax. Originally this was useful in the treatment of many neurological conditions. Doctors using this groundbreaking medicine noticed that, as a side effect, deep lines in patients' foreheads softened and their skin smoothed out. Since then, these agents have been used to successfully treat wrinkles and facial creases. Botox-type injectable agents are most often used on lines around the eyes (also known as "crow's feet") or frown and forehead lines.

Botox-type injectable agents are injected with a fine needle into specific muscles just under the skin and do not require anesthesia, resulting in only minor discomfort, not pain. In general, results are obtained within a day or two but the full effect may take up to 2-3 weeks to show and will generally last 4-6 months before a repeat treatment is recommended. The reason repeat treatment may be recommended is that muscle action eventually returns and the wrinkles begin to reappear. As treatments are continued the return of wrinkles or lines generally becomes less severe over time since the muscles are being virtually trained to relax.

For years, Botox® has been approved to help control and reduce the appearance of wrinkles on the forehead, help reduce migraine headaches, and alleviate excessive sweating. The FDA has also approved Botox® for treating canthal lines, or crow's feet, the wrinkles that form at the corners of the eyes. For patient's seeking a smoother appearance, Botox® can minimize the appearance of canthal lines for three to six months. Botox® can also be used for a non-surgical neck lift. Injecting the neck's platysma muscle, the thickness and position of which can effect a person's visible signs of aging, relaxes it and reduces the appearance of neck banding or "turkey neck." Botox® injections can also be used for non-surgical breast job, also known as Breastox, increasing the cup size and perkiness of the breasts. Injecting Botox® into the pectoral muscles causes them to relax and places the burden on the shoulder and chest muscles. The effect is the appearance of having larger, perkier breasts, with results lasting around 6 months.

Additionally, Botox® may be useful in reducing or eliminating the appearance of large facial pores or healing acne scars. The expansion of the pores and shaping of other facial aberrations are controlled by small muscles. Botox® helps to both relax these muscles and tighten the skin, resulting in the desired lessening or elimination of large pores. Small amounts of Botox® are injected directly under the skin, in the upper-most layers. This can most commonly be done along the cheeks, nose, and forehead. Also, excessive sweating, an annoying condition which can also make a person smell bad, can also be effectively treated using Botox®. Sweat glands have to receive a certain chemical signal in order to produce sweat. Botox® blocks this signal, thus reducing the amount of sweat that a person exudes. Botox® is injected into the parts of the body that regularly sweat a lot, such as the hands. And while sweating is stopped in the injection locations, the body can still sweat elsewhere, which is essential because sweating helps keep the body cool.

Facial Slimming and jaw reduction can be accomplished by applying Botox® to the masseter (chewing muscle), causing the muscle to become smaller and therefore resulting in a thinner facial appearance. When combined with facial fillers, which can be used to enhance the cheekbones, a contoured look can be achieved. If the jawline is too masculine, this method can also be used to reduce the jawline for a softer, more feminine appearance.

B. Treatment with Dermal Fillers

Certain cosmetic procedures utilize dermal fillers, also called injectable dermal fillers. Volume loss in the hands can be treated using dermal fillers. Radiesse® is the first and only FDA-approved product to correct volume loss in hands. While other dermal fillers provide excellent results for the face, Radiesse® has proven to be the most successful at restoring volume in the hands, with the longest lasting results. Using a fine needle, Radiesse® is injected into the hands, resulting in smooth, wrinkle-free, and most importantly, ageless hands. Radiesse can also be used to reduce cellulite by injection into cellulite dimples, causing the skin to appear fuller and smoother.

A non-surgical nose job can be accomplished by injecting a dermal filler, for example Restylane®, Bellafill® or Juvederm®, into the precise area of the nose to hide bumps and contour areas for the desired shape. Dermal fillers can also be used to create fuller lips, or one lip (generally the top lip) larger than the other lip. Additional cosmetic procedures that utilize a dermal filler (or a combination of dermal fillers) include cheek augmentation, chin sculpting, correction of dark undereye circles, and repair of "crow's feet."

C. Treatment with Other Cosmetic Agents

Certain cosmetic procedures utilize other cosmetic agents, which are detailed above. A breast lift (termed a "Vampire BreastLift") is accomplished by injecting PRP into the breast tissue to encourage multipotent stem cells to repair and increase fatty tissue, resulting in fuller and younger-looking breasts. Scar repair (termed "Vampire Scar Repair") is accomplished by injecting PRP into the skin at the location of the scar to rejuvenate and heal the skin, increase collagen, and generate new blood flow. Hair growth (termed "Vampire Hair Growth") is accomplished by injecting PRP into the scalp and hairline to reverse hair miniaturization and stimulate the growth of follicles.

Ultherapy® (or in certain cases dermal fillers) can be used to perform a non-surgical Brazilian Butt Lift. Ultherapy® is used around the buttocks to help achieve greater contour and stimulate collagen growth for a fuller appearance. Dermal fillers can fill pockets and wrinkles, reduce cellulite, and provide a smoother and more shapely appearance to the buttocks.

D. Combination Treatments

Certain cosmetic procedures utilize a combination of two or more cosmetic agents to produce the desired effect. For example, a face lift (termed a "Vampire FaceLift") is accomplished using a hyaluronic dermal filler and PRP. A facial (termed a "Vampire Facial") is accomplished by injecting PRP with a micro-needling technique into the forehead and around the cheeks to rejuvenate the skin. A non-surgical brow lift can be accomplished using Botox-type agents, dermal fillers, Ultherapy®, or a combination thereof.

III. Medical Agents

A number of different medical agents can be used in the practice of the claimed medical procedures. Although certain of these medical agents are described in greater detail below, inclusion of these agents is not meant to be exhaustive of the medical agents that can be used in this disclosure.

A number of medical agents comprising botulinum toxin type A are available for use in a variety of medical procedures. In general these agents are referred to as "Botox-type injectables." Botulinum toxin type A is an acetylcholine release inhibitor that blocks neuromuscular transmission by binding to acceptor sites on motor nerve terminals, entering the nerve terminals, and inhibiting the release of acetylcholine. Botulinum toxin type A produces partial chemical denervation of the muscle, resulting in a localized reduction in muscle activity.

The most popular of these medical agents is Botox® (onabotulinumtoxinA), which is purified botulinum toxin type A, produced from fermentation of the bacterium *Clostridium botulinum* type A, Hall Strain, and is intended for intramuscular use. It is purified from the culture solution by dialysis and a series of acid precipitations to a complex consisting of the neurotoxin, and several accessory proteins.

Other Botox-type injectable medical agents include, but are not limited to, Dysport® (abobotulinumtoxinA) and Xeomin® (incobotulinumtoxinA).

IV. Medical Procedures

A wide variety of medical procedures utilize Botox-type injectable agents to treat a variety of different medical conditions, as detailed below.

Medical agents comprising botulinum toxin type A can be used to treat migraine and other types of headaches, including, but not limited to, tension-type, chronic, cluster headaches, and occipital neuralgia, cervical dystonia (CD), blepharospasm, and pain management for fibromyalgia and increased muscle stiffness in elbow, wrist and finger muscles in adults with upper limb spasticity, increased muscle stiffness in calf muscles in children 2 years of age or older with lower limb spasticity.

Botox-type injectable medical agents comprise a purified botulinum toxin type A protein that causes tensed muscles to relax. These medical agents are injected with a fine needle into specific muscles just under the skin and do not require anesthesia, resulting in only minor discomfort, not pain. In general, results are obtained within a day or two but the full effect may take up to 2-3 weeks to show and will generally last 4-6 months before a repeat treatment is recommended. In the treatment of certain conditions, repeated injections over the span of weeks, for example 10, 12 or 15 weeks or longer is generally recommended. The reason repeat treatment may be recommended is that muscle action eventually returns. As treatments are continued the muscles are being virtually trained to relax.

EXAMPLES

Example 1

Injectable fillers are a transforming, modern way to enhance a patient's aesthetics through plumping up surface depressions, furrows, and wrinkles, such as the nasolabial folds. The universal technique of injecting fillers has been implemented in a way of having a patient seated, which as a result relaxes a patient's muscles, essentially making the lines less prominent. In this Example, pictures are provided of a patient in a seated (FIG. 1A) and standing (FIG. 1B) position to observe any difference of prominence, specifically in this case, of the nasolabial folds. These pictures were taken from a consistent distance and in similar lighting. The pictures were also taken within the same time frame, and the posture of the patient is consistent in both the standing and sitting position.

Three principle factors that play a role in the reduced prominence of the volume loss of the nasolabial folds in the sitting posture include: the lack of the effects of gravity; the relaxation of muscles; and the relaxation of the spine, which adds the element of a kyphotic posture.

Three principle factors that play a role in the upright standing position include: the increasing effects of gravity; the erection of the spine along with the head; and the hemodynamic effects of the body. The patient having their spine and head erect allows for accuracy of symmetry when observing the face. The hemodynamics effects are crucial not only medically but aesthetically as well. Having a patient stand upright induces an upright hemodynamic response causing more augmented body loss.

In FIG. 1A, Patient A is in the sitting position, exemplifying the relaxing of her muscles, viewing the injector. In FIG. 1B, Patient A is in the standing position, and the augmented volume loss of the nasolabial folds is more notable as compared to when Patient A is in the sitting position (FIG. 1A).

Having the patient in the standing position enables the injector to fill the problematic areas with volume loss more efficiently. In a standing, upright position, the augmentation of volume loss of the nasolabial folds, or other areas needing treatment, are more visible, ensuring an accurate injection.

Example 2

In this Example, pictures are provided of a second patient in a seated (FIG. 2A) and standing (FIG. 2B) position to observe any difference of prominence, specifically in this case, of the nasolabial folds. These pictures were taken from a consistent distance and in similar lighting. The pictures were also taken within the same time frame, and the posture of the patient is consistent in both the standing and sitting position.

Figure 2A:
FIG. 2A and FIG. 2B: A second patient is shown in the sitting (FIG. 2A) and standing (FIG. 2B) position, highlighting the difference in appearance of the nasolabial folds in the sitting and standing position.
Figure 2B:

In FIG. 2A, Patient B is in the sitting position, exemplifying the relaxing of her muscles, viewing the injector. In FIG. 2B, Patient B is in the standing position, notably exhibiting a more prominent left nasolabial fold as compared to when Patient B is in the sitting position (FIG. 1A).

Once again, having the patient in the standing position enables the injector to fill the problematic areas with volume loss more efficiently. In a standing, upright position, the augmentation of volume loss of the nasolabial folds, or other areas needing treatment, are more visible, ensuring an accurate injection.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of." As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property or properties, method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about," "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%, or indicate that a value includes the standard deviation of error for the device or method being employed to determine the value.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the methods described herein without departing from the concept, spirit and scope of this disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of this disclosure as defined by the appended claims.

The invention claimed is:

1. A method of administration of a dermal filler to a patient in need thereof, the patient having a pair of feet, the method comprising injecting said dermal filler to said patient while said patient is in a standing position on said pair of feet.

2. The method of claim 1, wherein said dermal filler comprises injectable hyaluronic acid.

3. The method of claim 1, wherein said dermal filler comprises injectable poly-L-lactic acid.

4. The method of claim 1, wherein said dermal filler comprises collagen and polymethylmethacrylate.

5. The method of claim 1, wherein said cosmetic agent stimulates collagen production in said patient.

6. The method of claim 1, wherein said dermal filler further comprises botulinum toxin type A.

7. The method of claim 1 further comprising administration of a second cosmetic agent to said patient.

8. The method of claim 7, wherein said second cosmetic agent comprises Botulinum toxin type A.

9. A method for administering an injectable dermal filler to a facial area of a patient in need thereof, the patient having a pair of feet, the method comprising: causing an injection of said dermal filler to said facial area of said patient as said patient is in a standing position on said pair of feet during said injecting.

* * * * *